US00PP15601P2

(12) United States Plant Patent
Garland

(10) Patent No.: US PP15,601 P2
(45) Date of Patent: Mar. 1, 2005

(54) ***GERANIUM* PLANT NAMED 'SOLSTICE PURPLE'**

(50) Latin Name: *Pelargonium grandiflorum*
Varietal Denomination: Solstice Purple

(75) Inventor: Lin Garland, Dereham (GB)

(73) Assignee: Floranova Ltd., Dereham (GB)

( * ) Notice: Subject to any disclaimer, the term of this patent is extended or adjusted under 35 U.S.C. 154(b) by 0 days.

(21) Appl. No.: 10/822,984

(22) Filed: Apr. 13, 2004

(51) Int. Cl.[7] ..... A01H 5/00
(52) U.S. Cl. ..... Plt./324
(58) Field of Search ..... Plt./324

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Geranium* plant named 'Solstice Purple', characterized by its upright, outwardly spreading and mounded growth habit; freely branching habit; dense and full plant habit; freely flowering habit; red purple and dark purple-colored flowers; and no requirement for vernalization.

1 Drawing Sheet

Botanical classification/cultivar designation: *Pelargonium grandiflorum* cultivar Solstice Purple.

BACKGROUND OF THE INVENTION

The present invention relates to a new and distinct cultivar of *Geranium* plant, commercially known as Regal Geranium, botanically known as *Pelargonium grandiflorum,* and hereinafter referred to by the name 'Solstice Purple'.

The new Regal Geranium is a product of a planned breeding program conducted by the Inventor in Foxley, Dereham, Norfolk, United Kingdom. The objective of the breeding program is to develop new Regal Geranium cultivars with compact growth habit, early flowering habit, numerous small flowers, and interesting flower and foliage colors that do not require vernalization for flowering.

The new Regal Geranium originated from a cross-pollination made by the Inventor in June, 2001 of a proprietary *Pelargonium grandiflorum* selection identified as code number RPOLB4, not patented, as the female, or seed, parent with a proprietary *Pelargonium grandiflorum* selection identified as code number RPFTJ24, not patented, as the male, or pollen, parent. The cultivar Solstice Purple was discovered and selected by the Inventor as a flowering plant from within the progeny from this cross-pollination in a controlled environment in Foxley, Dereham, Norfolk, United Kingdom.

Asexual reproduction of the new cultivar by terminal cuttings at Foxley, Dereham, Norfolk, United Kingdom, since June, 2002 has shown that the unique features of this new Regal Geranium are stable and reproduced true to type in successive generations of asexual reproduction.

SUMMARY OF THE INVENTION

The following traits have been repeatedly observed and are determined to be the unique characteristics of 'Solstice Purple'. These characteristics in combination distinguish 'Solstice Purple' as a new and distinct Regal Geranium cultivar:

1. Upright, outwardly spreading and mounded growth habit.
2. Freely branching habit; dense and full plant habit.
3. Freely flowering habit.

4. Red purple and dark purple-colored flowers.
5. No requirement for vernalization.

Plants of the new Regal Geranium differ from plants of the female parent selection in the following characteristics:

1. Plants of the new Regal Geranium are more uniform than plants of the female parent selection.
2. Plants of the new Regal Geranium flower earlier than plants of the female parent selection.
3. Plants of the new Regal Geranium and the female parent selection differ in flower color as plants of the female parent selection have purple-colored flowers.

Plants of the new Regal Geranium differ from plants of the male parent selection in the following characteristics:

1. Plants of the new Regal Geranium are more uniform than plants of the male parent selection.
2. Plants of the new Regal Geranium are more compact than plants of the male parent selection.
3. Plants of the new *Geranium* are more freely branching than plants of the male parent selection.

The new Regal Geranium can be compared to the cultivar, Burghi, not patented. However, in side-by-side comparisons conducted in Foxley, Norfolk, United Kingdom, plants of the new Regal Geranium differed from plants of the cultivar Burghi in the following characteristics:

1. Plants of the new Regal Geranium were more compact than plants of the cultivar Burghi.
2. Plants of the new Regal Geranium were more freely branching than plants of the cultivar Burghi.
3. Plants of the new Regal Geranium had smaller flowers than plants of the cultivar Burghi.
4. Plants of the new Regal Geranium did not require vernalization for flowering whereas plants of the cultivar Burghi required vernalization for flowering.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Flower and foliage colors in the photographs may differ slightly from the color values cited in the detailed botanical description which accurately describe the colors of the new Regal Geranium.

The photograph at the bottom of the sheet comprises a side perspective view of a typical flowering plant of 'Solstice Purple'.

The photograph at the top of the sheet comprises a close-up view of typical flowers of 'Solstice Purple'.

DETAILED BOTANICAL DESCRIPTION

The cultivar Solstice Purple has not been observed under all possible environmental conditions. The phenotype may vary somewhat with variations in environment such as temperature and light intensity, without, however, any variance in genotype. The aforementioned photographs and following observations and measurements describe plants grown in Lompoc, Calif., under commercial practice in a polycarbonate-covered greenhouse during the winter with day temperatures ranging from 18 to 24° C., night temperatures ranging from 16 to 18° C. and light levels ranging from 4,000 to 8,000 foot-candles. Plants used for the photographs and description were about 16 weeks from planting rooted cuttings and were grown in 11.25-cm containers. In the following description, color references are made to The Royal Horticultural Society Colour Chart, 1995 Edition, except where general terms of ordinary dictionary significance are used.

Botanical classification: *Pelargonium grandiflorum* cultivar Solstice Purple.

Parentage:

*Female, or seed, parent.*—Proprietary *Pelargonium grandiflorum* selection identified as RPOLB4, not patented.

*Male, or pollen, parent.*—Proprietary *Pelargonium grandiflorum* selection identified as RPFTJ24, not patented.

Propagation:

*Type cutting.*—Terminal cuttings.

*Time to initiate roots.*—About one week at 21° C.

*Time to develop roots.*—About three weeks at 21° C.

*Root description.*—Fine; white in color.

*Rooting habit.*—Freely branching.

Plant description:

*General appearance.*—Upright and outwardly spreading; mounded growth habit; inverted triangle.

*Growth and branching habit.*—Vigorous and freely branching with about six lateral branches per plant; dense and full plant habit. Pinching is typically not required.

*Plant height* (*to top of foliage*).—About 19 cm.

*Plant height* (*to top of flowering umbels*).—About 28 cm.

*Plant width.*—About 26 cm.

*Lateral branches.*—Length: About 17 cm. Diameter: About 6 mm. Internode length: About 1.75 cm. Texture: Pubescent. Color: 146A.

*Foliage description.*—Arrangement: Alternate, simple. Length: About 6 cm. Width: About 8.5 cm. Shape: Broadly deltoid, three-lobed. Apex: Acute. Base: Truncate to slightly cordate. Margin: Irregularly serrate. Venation: Palmate. Texture, upper and lower surfaces: Leathery, tough; pubescent.

*Color.*—Developing and fully expanded foliage, upper surface: 147A. Developing and fully expanded foliage, lower surface: 147B. Venation, upper surface: 147B. Venation, lower surface: 148C.

*Petiole.*—Length: About 1.6 cm. Diameter: About 4 mm. Texture, upper and lower surfaces: Glabrous. Color, upper and lower surfaces: 147B to 147C.

Flower description:

*Flower arrangement and type.*—Single rounded flowers arranged in hemispherical umbels arising from apical leaf axils. Umbels displayed above the foliage. At full flowering, usually about eight open and developing umbels per plant. Umbels persistent. Flower not fragrant.

*Flowering season.*—Year-round under greenhouse conditions; vernalization is not required for flowering. In the garden, flowering is continuous from spring until fall. Plants start flowering about ten weeks after planting.

*Flower longevity.*—Flowers last about one week on the plant.

*Umbels/flowers.*—Height: About 6.5 cm. Diameter: About 9.5 cm. Number of flowers and flower buds per umbel: Freely flowering, about nine. Flower diameter: About 6 cm. Flower depth (height): About 3.8 cm.

*Flower buds.*—Length: About 2 cm. Diameter: About 7 mm. Shape: Elongated ovoid. Color: 187B.

*Petals.*—Quantity: About five per flower arranged in a single whorl. Length, upper two petals: About 4 cm. Length, lower three petals: About 3.7 cm. Width, upper two petals: About 3.3 cm. Width, lower three petals: About 2.1 cm. Shape: Obovate. Apex: Rounded. Base: Attenuate. Margin: Entire. Texture, upper and lower surfaces: Smooth; satiny. Color: When opening, upper surface: 187A; towards the margins, brighter than 187B. When opening, lower surface: 187B. Fully opened, upper surface: Towards the margins, 74A; towards the center, 53A; central spot, 187A; base, 187A to 187B; venation, 187A. Fully opened, lower surface: Towards the margins, 187B to 187C; center and base, 187A to 187B; venation, 187A.

*Sepals.*—Quantity: Five per flower arranged in a single whorl. Length: About 1.6 cm. Width: About 7 mm. Shape: Elliptic to lanceolate. Apex: Acuminate. Base: Attenuate. Margin: Entire. Texture, upper and lower surfaces: Pubescent. Color, upper and lower surfaces: 144A.

*Peduncle* (*umbel stem*).—Length: About 3.7 cm. Diameter: About 2 mm. Angle: Upright to about 30° from lateral branch. Strength: Strong. Texture: Pubescent. Color: 144A.

*Pedicel* (*individual flower stem*).—Length: About 2.4 cm. Diameter: About 1.5 mm. Angle: About 45° from vertical. Strength: Strong. Texture: Pubescent. Color: 144A.

*Reproductive organs.*—Androecium: Anther quantity: Five per flower. Anther shape: Elongated oblong. Anther size: About 1.5 mm by 3 mm. Anther color: 187B. Pollen amount: Moderate. Pollen color: 31A. Gynoecium: Pistil quantity: One per flower. Pistil length: About 2.2 cm. Stigma shape: Five or six-parted, star-shaped; reflexed. Stigma color: 187A. Style length: About 1.4 cm. Style color: 187A. Ovary color: 194C.

*Seed/fruit.*—None observed.

Disease/pest resistance: Resistance to pathogens and pests common to Regal Geraniums has not been observed.

It is claimed:

1. A new and distinct cultivar of *Geranium* plant named 'Solstice Purple', as herein illustrated and described.

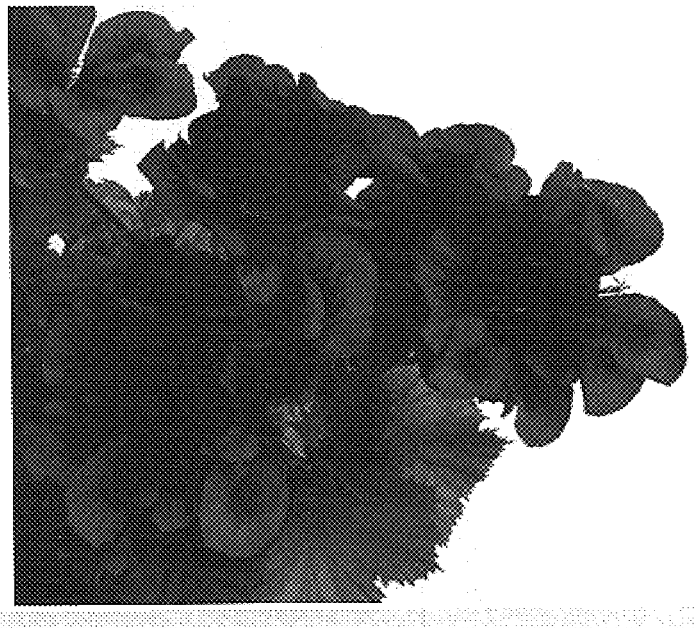
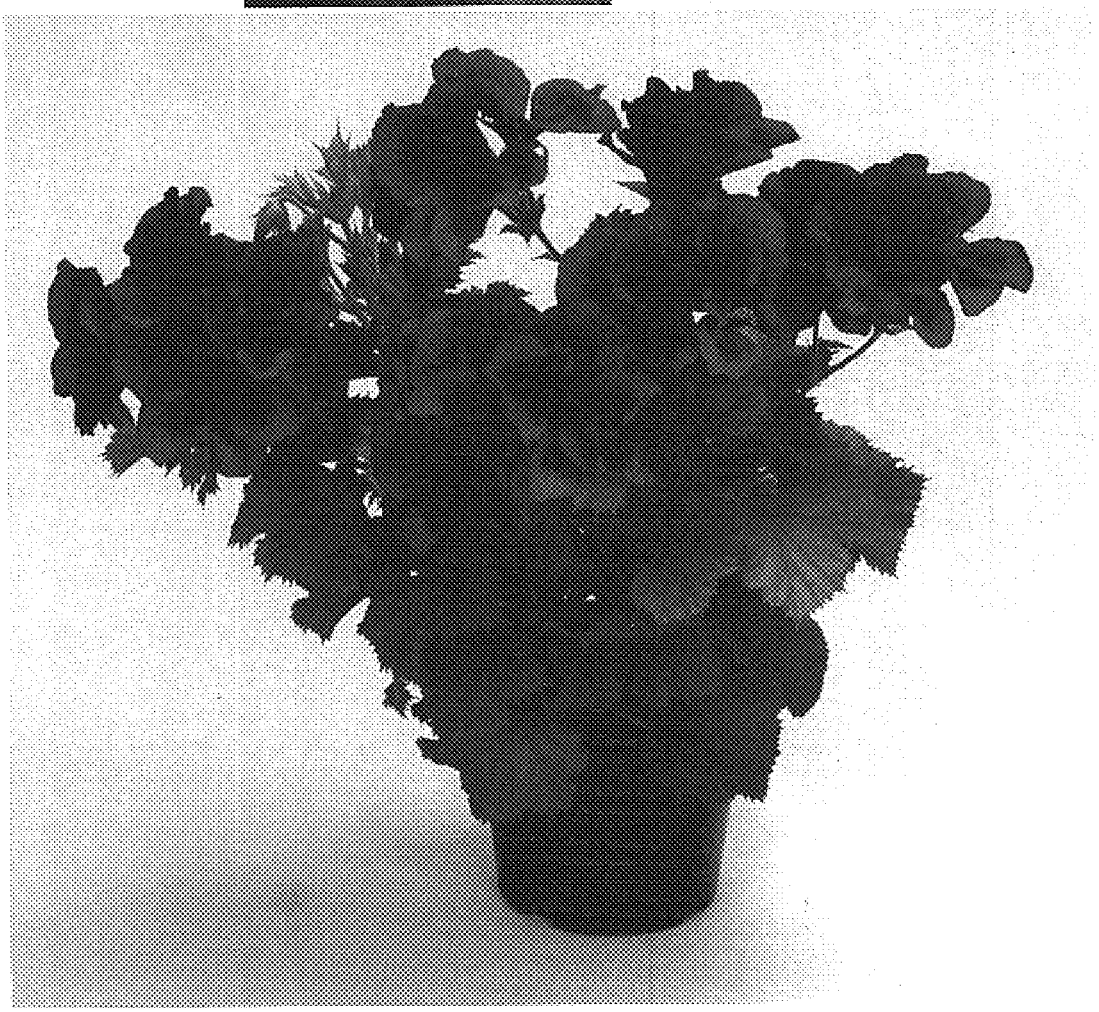

* * * * *